United States Patent [19]

Weisheit et al.

[11] Patent Number: 5,763,281

[45] Date of Patent: Jun. 9, 1998

[54] METHOD AND REAGENT FOR THE DETERMINATION OF IRON

[75] Inventors: Ralph Weisheit, Weilheim; Renate Luz, Tutzing, both of Germany

[73] Assignee: Boehringer Mannheim GmbH, Mannheim, Germany

[21] Appl. No.: 680,255

[22] Filed: Jul. 11, 1996

Related U.S. Application Data

[63] Continuation of Ser. No. 376,554, Jan. 20, 1995, abandoned.

[30] Foreign Application Priority Data

Jan. 21, 1994 [DE] Germany ............... 44 01 754.5

[51] Int. Cl.⁶ ............................ G01N 33/52; G01N 33/90
[52] U.S. Cl. ........................ 436/74; 436/43; 436/73; 436/84; 436/166; 436/174; 436/175; 422/56; 422/61
[58] Field of Search ............................. 436/43, 73, 74, 436/84, 166, 174, 175; 422/56–58, 61

[56] References Cited

U.S. PATENT DOCUMENTS

| | | | |
|---|---|---|---|
| 3,943,954 | 3/1976 | Flournoy | 137/13 |
| 4,579,825 | 4/1986 | Siedel et al. | 436/175 |
| 4,961,970 | 10/1990 | Siedel et al. | 436/84 |
| 5,149,633 | 9/1992 | Vogt et al. | 436/175 X |
| 5,219,760 | 6/1993 | Herrmann et al. | 436/84 |

FOREIGN PATENT DOCUMENTS

| | | |
|---|---|---|
| 0404590A3 | 12/1990 | European Pat. Off. |
| 61-95247 | 5/1986 | Japan |
| 61-95247 | 5/1996 | Japan |

OTHER PUBLICATIONS

S. Tajima et al. *Arch. Biochem. Biophys.* 1979, 198, 137–144.

H. Hoffmann et al. *J. Colloid. Interfac. Sci.* 1981, 80, 237–254.

R. Jha et al *J. Chem. Soc., Faraday Trans.* 1993, 89, 3465–3469.

*Primary Examiner*—Arlen Soderquist
*Attorney, Agent, or Firm*—Nikaido Marmelstein Murray & Oram LLP

[57] ABSTRACT

In order to determine iron in serum by releasing the bound iron through addition of a protein denaturing agent, reduction of the released iron to $Fe^{2+}$, addition of a color reagent solution and photometric measurement of the color complex that forms, a mixture of a denaturing agent containing urea or a urea derivative and a fatty alcohol polyglycol ether are added to the sample solution.

18 Claims, 4 Drawing Sheets

METHOD AND REAGENT FOR THE DETERMINATION OF IRON

This application is a continuation of application Ser. No. 08/376,554 filed Jan. 20, 1995, now abandoned.

The invention concerns a method for the determination of iron in serum with release of bound iron by addition of protein denaturing agent, reduction of the released iron to $Fe^{2+}$, addition of a colour reagent solution and photometric measurement of the colour complex that is formed as well as a reagent combination which is suitable for the measurement of lipaemic sera even without addition of clearing surfactant mixtures.

Disturbances of iron metabolism and in particular iron deficiency and iron resorption disorders are widespread above all in the female population. The detection of iron in body fluids and in particular in serum is therefore among one of the standard determinations in medical analytics. Iron is supplied with the diet and taken up via the mucous membrane of the intestine. While bound to transferrin in the trivalent state, it is then transported to the bone marrow where it is mainly incorporated into haemoglobin. If too little iron is absorbed then anaemic symptoms occur.

The determination of iron in serum is among one of the most frequently carried out trace element analyses in clinical diagnostics. Various methods are known for this. Thus a method is described in Clin. Chem. 26 (1980) 327–331 in which trivalent iron bound to transferrin in the form of a carbonate complex is released in a strongly acidic environment. A disadvantage of this method is that the strongly acidic reagents have caustic and corroding properties. In order to obviate this disadvantage it is for example known from Clin. Chem. 23 (1977) 237–240 and from Z. Clin. Chem. 3 (1965) 96–99 that protein denaturing agents such as concentrated guanidinium chloride or anionic detergents can be used to release iron.

In the known embodiments of these methods erroneous measurements occur when determining iron in turbid lipaemic sera. Neither guanidinium chloride nor anionic detergents have a clearing capacity sufficient to achieve a complete elimination of turbidity.

In order to solve this problem it was suggested in EP-A-0 130 537 that a mixture of non-ionic and anionic detergents be used to release the iron in a weakly acidic medium. However, it was found that when using these detergents lipaemic sera were indeed cleared rapidly and completely but an increase in turbidity is observed in the case of sera with an increased content of immunoglobulin (gammopathy sera) which can falsify the measured result. In addition the recovery in strongly haemolytic sera is not completely satisfactory.

In EP-A-0 343 592 it is suggested that to solve this problem a first solution of a denaturing agent at a concentration of 1–8 mol/l be added to the serum, after addition of the first solution a turbidity measurement is carried out, subsequently a second solution is added which contains the colour reagent and also a denaturing agent at a concentration of 1–8 mol/l and afterwards the colour complex is determined and in order to determine the amount of iron the measured value for turbidity is subtracted from the measured value of the colour complex solution. A disadvantage of this method is that precipitations can occur in the second solution which are probably composed of a complex of the dye and the denaturing agent. The concentration of the dye in this solution must therefore be reduced which can result in interferences due to EDTA contamination and false measurements due to a non-linear reaction course in samples with a low iron content.

The object was therefore to create a method and a reagent for the determination of iron in a biological sample in which, on the one hand no aggressive components have to be used and on the other hand, interference by lipaemic sera can be avoided without the measurement being interfered with by haemolytic samples or sera with an increased content of immunoglobulin. For reasons of automatability and rationalization it is additionally desirable that no prior deproteination of the sample should be necessary.

This object is achieved according to the invention by a method for the determination of iron in a biological sample with release of the bound iron by addition of a protein denaturing agent, reduction of the released iron to $Fe^{2+}$, addition of a colour reagent solution and photometric measurement of the colour complex that forms which is characterized in that a denaturing agent containing urea or a urea derivative and a fatty alcohol polyglycol ether are added to the biological sample. As biological sample blood serum or plasma, in particular plasma of heparinized blood could be used. Serum is the preferred sample.

The invention is based on the finding that a turbidity can be avoided when adding the colour reagent, by a combination of a denaturing agent containing urea or a urea derivative and of a single, very specific detergent—a fatty alcohol polyglycol ether. This enables a measurement of lipaemic sera as well as of gammopathy sera that is free from interference. In order to avoid turbidities which occur in lipaemic sera it is no longer necessary to use detergent combinations as described in EP-A-0 130 537, DE-A-27 24 757 or DE-A-37 29 502.

It is known that various protein denaturing agents can be added to detach iron from binding proteins and in particular from ferritin. Urea or urea derivatives such as for example the salts of the cation guanidinium are suitable for protein denaturation within the scope of the invention and the salts guanidinium chloride, guanidinium acetate, guanidinium thiocyanate or guanidinium sulfate are particularly preferred.

The denaturing agent is used in a first solution of the iron test according to the invention in combination with the fatty alcohol polyglycol ether. The concentration of the denaturing agent in the first solution of the iron test according to the invention must be relatively high and be between 1 and 8 mol/l. The best results are obtained with concentrations between 4 and 6 mol/l. At concentrations under 1 mol/l, the detachment of iron from transferrin becomes increasingly slower. The preferred concentration range for the particularly preferred guanidinium chloride is between 1 and 6 mol/l, particularly preferably between 4 and 5 mol/l.

The fatty alcohol polyglycol ethers that are used are those whose degree of ethoxylation exhibits more than 4 and up to 7 ethoxy units and for the production of which a branched or unbranched fatty alcohol has been used. A fatty alcohol with an average of 9–11 carbon atoms is preferably used. Particularly preferred fatty alcohol polyglycol ethers are for example Lutensol® ON 50, Lutensol® ON 60, Imbentin®-C/91/35, Imbentin®-AG/100/050. The specification of a degree of ethoxylation is understood as the average degree of ethoxylation of a batch since the fatty alcohol polyglycol ethers are usually a mixture of substances with slightly different degrees of ethoxylation. Lutensol® (decylpolyethylene glycol ether) is a trademark of BASF AG, Germany, and Imbentin® is a trademark of Dr. W. Kolb AG, Switzerland. Lutensol® ON 50 has an average of 5 ethoxy units and Lutensol® ON 60 an average of 6 ethoxy units. Imbentin®-C/91/35 is a mixture of alkyl polyethylene glycol ethers with 9 to 11 carbon atoms in the alkyl residue and 5 ethoxy units in the polyethylene glycol residue. Imbentin®-AG/100/500 is decyl polyethylene glycol ether with an average of 5 ethoxy units in the polyethylene glycol residue.

The concentration of the fatty alcohol polyglycol ether in the first solution of the iron test according to the invention must be at least 10 g/l. The concentration is preferably at least 30 g/l since in this case a more rapid clearing of lipaemic samples occurs. The upper concentration of the fatty alcohol polyglycol ether results from the technical upper limit i.e. the concentration at which the detergent no longer completely dissolves. A detergent concentration of 50 to 100 g/l is especially preferred. The use of the said fatty alcohol polyglycol ethers enables a complete clearing of lipaemic samples within a few minutes. Five minutes is usually adequate for the clearing. Hence the reagent can also be used for rapidly measuring automated analysers.

Surfactants with a lower or higher degree of ethoxylation than the fatty alcohol polyglycol ethers used according to the invention such as Tween®20, Genapol X-080, Oxetal ID 104, Thesit®, Lutensol® ON30, Triton®X-100 (polyoxyethylene $_{(9-10)}$p-t-octylphenol) are not suitable for clearing lipaemic samples in a reagent containing urea or a urea derivative.

In order to carry out the method according to the invention, the sample solution is preferably buffered in a weakly acidic range, particularly preferably in the range between pH 3.5 and pH 6. Compounds are suitable as buffer substances that have a pK value of 3.5 to 6 and do not complex iron. Acetate, phosphate or succinate buffers are for example suitable. A further preferred variant consists of firstly adjusting to an acidic pH value to release the iron, particularly preferably pH 2 to pH 6, and subsequently to re-buffer to a pH which gives an optimal colour yield with the colour system selected for the detection of iron. The pH values necessary for this are known to a person skilled in the art for example from Fielding, Methods in Hematology 1(Iron), 15–49 (1980).

Acetate buffer is preferably used as the buffer substance. The buffer is preferably used at a concentration of 20 to 500 mmol/l, particularly preferably of 50 to 150 mmol/l. The buffer substance can be included in the first solution of the iron test according to the invention which contains the denaturing agent and the fatty alcohol polyglycol ether. In addition the other solutions or the other solution of the iron test according to the invention can also be buffered.

In order to determine iron, a reducing agent such as ascorbic acid, dithionite or hydroxylamine is added to the sample solution in a known manner to reduce the released iron present in a trivalent form into the divalent form. The reducing agent may be added to the first solution together with the denaturing agent as well as to the second solution which additionally contains the colour system suitable for the detection of iron. The reducing agent is preferably added to the second solution.

Colour systems for the detection of iron are described for example in EP-A-0 228 060, Clin. Biochem. 14 (1981), 311–315 and Clin. Chem. 23 (1979), 237–240. Complexing agents of the ferroin type which yield a dye with iron that can be assayed photometrically are particularly suitable. Suitable substances are for example bathophenanthroline, ferene (3-(2-pyridyl)-5,6-bis(2-[furylsulfonic acid])-1,2,4-triazine disodium salt) and ferrozine (3'(2'-pyridyl)-5,6-diphenyl-1,2,4-triazine-sulfonic acid disodium salt). In this process the dye formation is proportional to the iron content of the sample and can be assayed photometrically in a well-known manner.

This invention enables for the first time the production of a reagent that is suitable for the photometric determination of iron even in very lipaemic biological samples which dispenses with a complete detergent system and uses only a single surfactant.

The invention therefore in addition concerns the use of a mixture of a denaturing agent containing urea or a urea derivative and of a fatty alcohol polyglycol ether to prevent interferences by lipaemia and gammopathy in the photometric determination of iron in a sample.

The effectiveness of the reagent in clearing lipaemic samples can be examined photometrically at a sample/reagent ratio of 1:5 to 1:25, preferably 1:10 to 1:15. In this case complete clearing is defined as when a solution of Intralipid® 20% (Kabi Pharmacia GmbH, Germany), a fat emulsion based on soya beans that has been further diluted with water in a ratio of 1:20, gives a maximum absorbance of 5 mA against the reagent solution as the blank value after five minutes at 37° C. at a wavelength of 578 nm and a path length of 1 cm.

The clearing can, however, also be examined on lipaemic biological samples by measuring the absorbance/time course (A/t) in which case it is then defined as being complete when the absorbance measured after five minutes differs by less than 5 mA and preferably less than 2 mA from the absorbance measured after 10 minutes.

In order to assess interference by lipaemia, the iron content of a biological sample supplemented with Intralipid® 20% is compared with the same sample that has, however, been admixed with water (analogous to Glick, Clin. Chem. 32 (1986), 470–475). An interference by lipaemia is present when the measured iron content of a mixture of one part by volume Intralipid® 20% and 19 parts by volume serum and the measured iron content of a mixture of 1 part by volume water and 19 parts by volume of the same serum differ by more than 5 µg/dl.

The invention in addition concerns a combination of reagents for the determination of iron in serum characterized by a first reagent containing 1 to 8 mol/l denaturing agent and at least 10 g/l fatty alcohol polyglycol ether and separate therefrom a second reagent containing 0.5 to 50 mmol/l dye in the form of aqueous solutions or suitable dry mixtures for their preparation. Both reagents or also only the first reagent can additionally contain 20 to 500 mmol/l buffer substance.

The second reagent can in addition already contain a reducing agent such as ascorbic acid, dithionite or hydroxylamine at a concentration of 40 to 200 mmol/l. The reducing agent can also be present at a higher concentration (e.g. 1000 mmol/l). However, there is then a risk that sparingly soluble degradation products (e.g. oxalate from ascorbic acid) are formed on long-term storage which can lead to reagent turbidity. Surprisingly it has turned out that the reducing agent in the second reagent is stable in the form of an aqueous solution. In the previously common reagent combinations for the determination of iron in serum the reducing agent usually has to be added shortly before using the liquid reagent.

The invention is elucidated in more detail by the following examples.

Example 1

The following reagents are used to determine iron in serum:

| Reagent 1: | |
|---|---|
| 4 mol/l | guanidinium hydrochloride |
| 0.15 mol/l | acetate buffer pH 5.0 |
| 0.100 mol/l | thiourea | fatty alcohol polyglycol ether in the respective concentrations given below.

| Reagent 2: | |
|---|---|
| 15 mmol/l | ferrozine |
| 0.1 mol/l | ascorbic acid |

The experiments were carried out on a Hitachi 717, Boehringer Mannheim GmbH.

20 μl sample was mixed with 250 μl reagent 1. 50 μl reagent 2 was added by pipette after 4.6 minutes incubation at 37° C. The absorbance 1 was determined shortly before adding reagent 2. Absorbance 2 was measured after 6 minutes. The difference in absorbance ΔA=A2−A1 can be determined from this. As an alternative A/t diagrams were plotted for a better illustration of the clearing.

In the first example the clearing was determined on the basis of A/t diagrams using various detergents in reagent 1 as exemplified by a human serum which was supplemented with Intralipid®20. The triglyceride content of the spiked human serum sample was ca. 2000 mg/dl. Fatty alcohol polyglycol ethers with 3 ethoxy units (Lutensol®ON 30), 5 ethoxy units (Lutensol®ON 50) and 8 ethoxy units (Genapol X-080) were used as detergents. Reagent 1 without detergent was used as a control. The results are shown in FIG. 1. It can be clearly seen that only the reagent according to the invention with a fatty alcohol polyglycol ether of 5 ethoxy units leads to a clearing of the lipaemic sample. The absorbance is already decreased to the zero value after ca. two minutes. A fatty alcohol polyglycol ether with 8 ethoxy units does not result in a clearing of the sample. The fatty alcohol polyglycol ether with 3 ethoxy units even leads to an increased turbidity of the sample.

Example 2

The experiment was carried out analogously to example 1. Various fatty alcohol polyglycol ethers according to the invention with 4.5 to 6 ethoxy units were used (Imbentin-E/V-177: 4.5 ethoxy units; Lutensol®ON 50: 5 ethoxy units; Imbentin-AG/100/50: 5 ethoxy units; Imbentin-C/91/35: 5 ethoxy units; Lutensol® ON 60: 6 ethoxy units).

The results are shown in FIG. 2. As can be clearly seen, all fatty alcohol polyglycol ethers according to the invention result in a rapid clearing of the sample in the case of a human serum that was supplemented with Intralipid (triglyceride content ca. 2000 mg/dl). All samples were cleared after ca. two minutes. Imbentin E/V-177 and Imbentin-AG/100/50 already resulted in a ccomplete clearing of the sample after one minute.

Example 3

Lutensol®ON 50 was used as an example to determine the influence of the concentration of detergent on the clearing of a human serum which was supplemented with Intralipid up to a triglyceride content of ca. 2000 mg/dl. The results are shown in FIG. 3. A concentration of 4% Lutensol®ON 50 already leads after ca. three minutes to a complete clearing of the sample. 5% Lutensol®ON 50 already leads to a complete clearing after ca. two minutes and 10% Lutensol®ON 50 already leads to a complete clearing of the sample after one minute.

As can be clearly seen even the very high concentration of 10% does not influence the colour development after adding reagent 2.

The experiment was carried out analogously to example 1.

Example 4

This example was used to demonstrate that not only samples artificially supplemented with Intralipid but also naturally occurring lipaemic human sera can be cleared with the reagent according to the invention. In this example a lipaemic human serum was used which had a triglyceride content of ca. 1000 mg/dl. The experiment was carried out analogously to example 1. 5% Lutensol®ON 50 was present as a detergent in reagent 1.

As can be clearly seen in FIG. 4, the addition of reagent 1 already leads to a complete clearing of the lipaemic human serum after two minutes.

Figure 1:
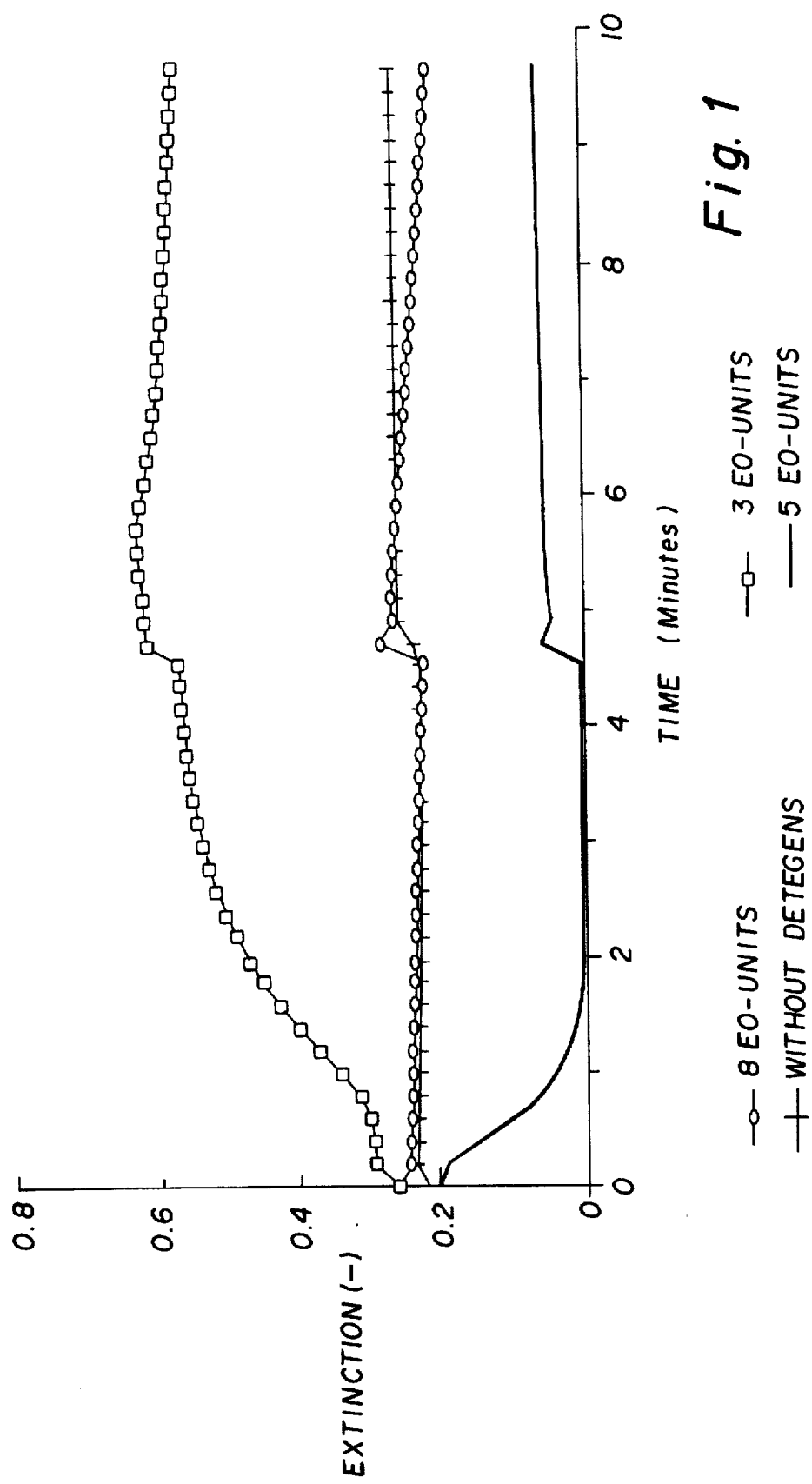
FIG. 1 shows the clearing of human serum which was supplemented with Intralipid® 20 by Lutensol® ON 30 (3 EO-Units), Lutensol® ON 50 (5 EO-Units) and Genapol X-080 (8 EO-Units) as described in example 1.
Figure 2:
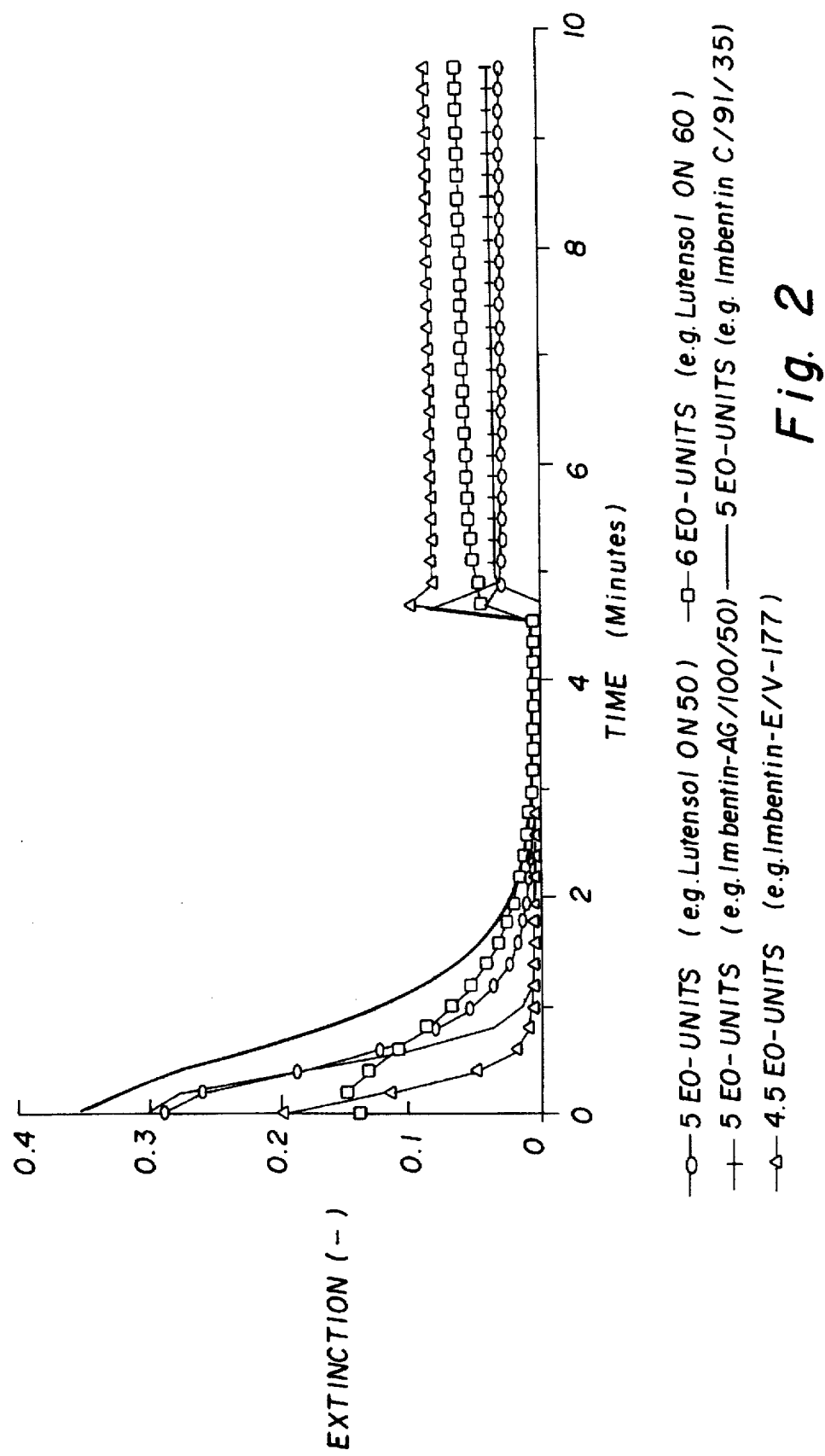
FIG. 2 shows the clearing of human serum which was supplemented with Intralipid® 20 by various fatty alcohol polyglycol ethers with 4.5 to 6 ethoxy units (EO-Units) as described in example 2.
Figure 3:
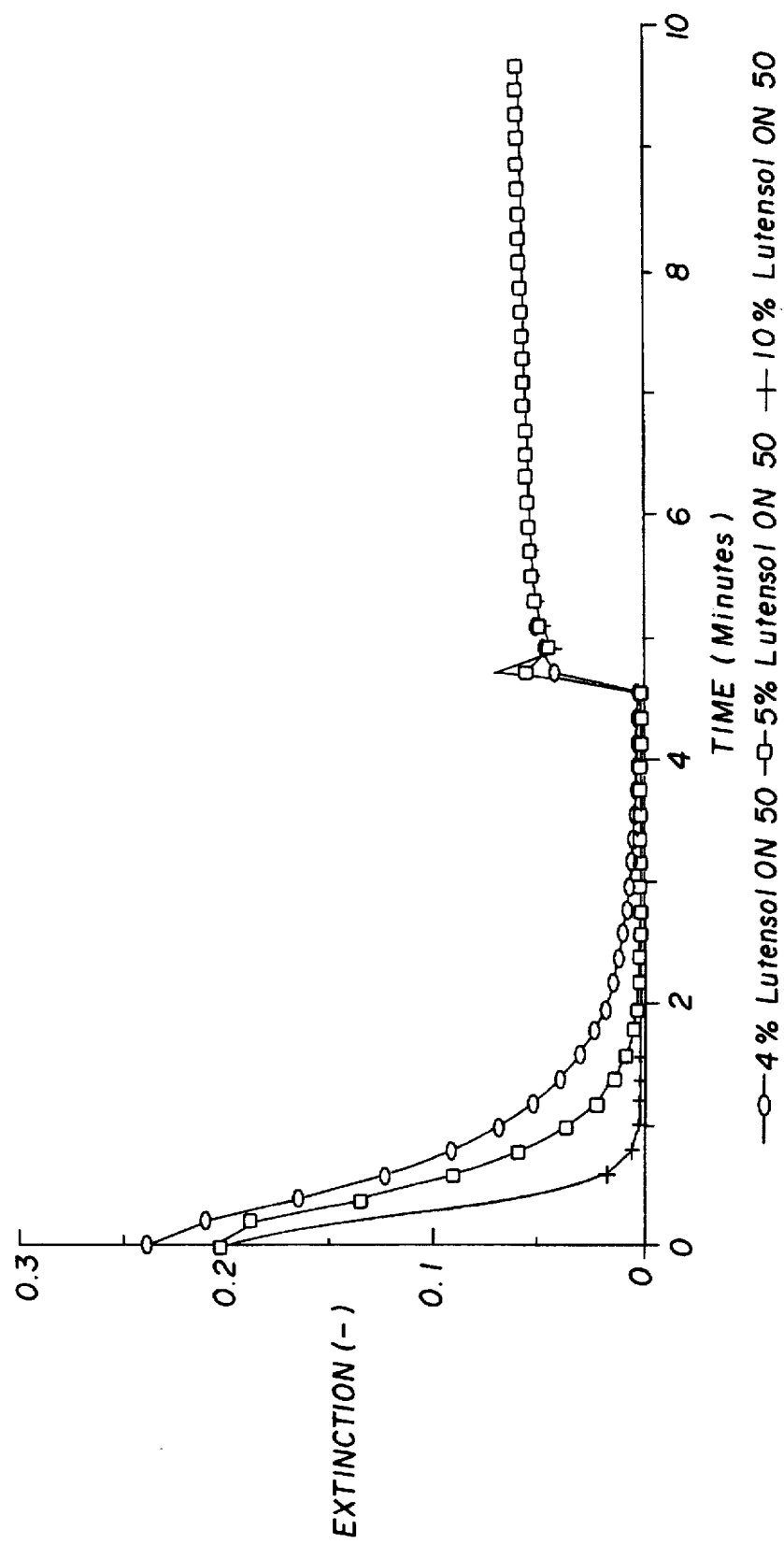
FIG. 3 shows the clearing of a sample supplemented with Intralipid® 20 by various concentrations of Lutensol® ON 50 as described in example 3.
Figure 4:
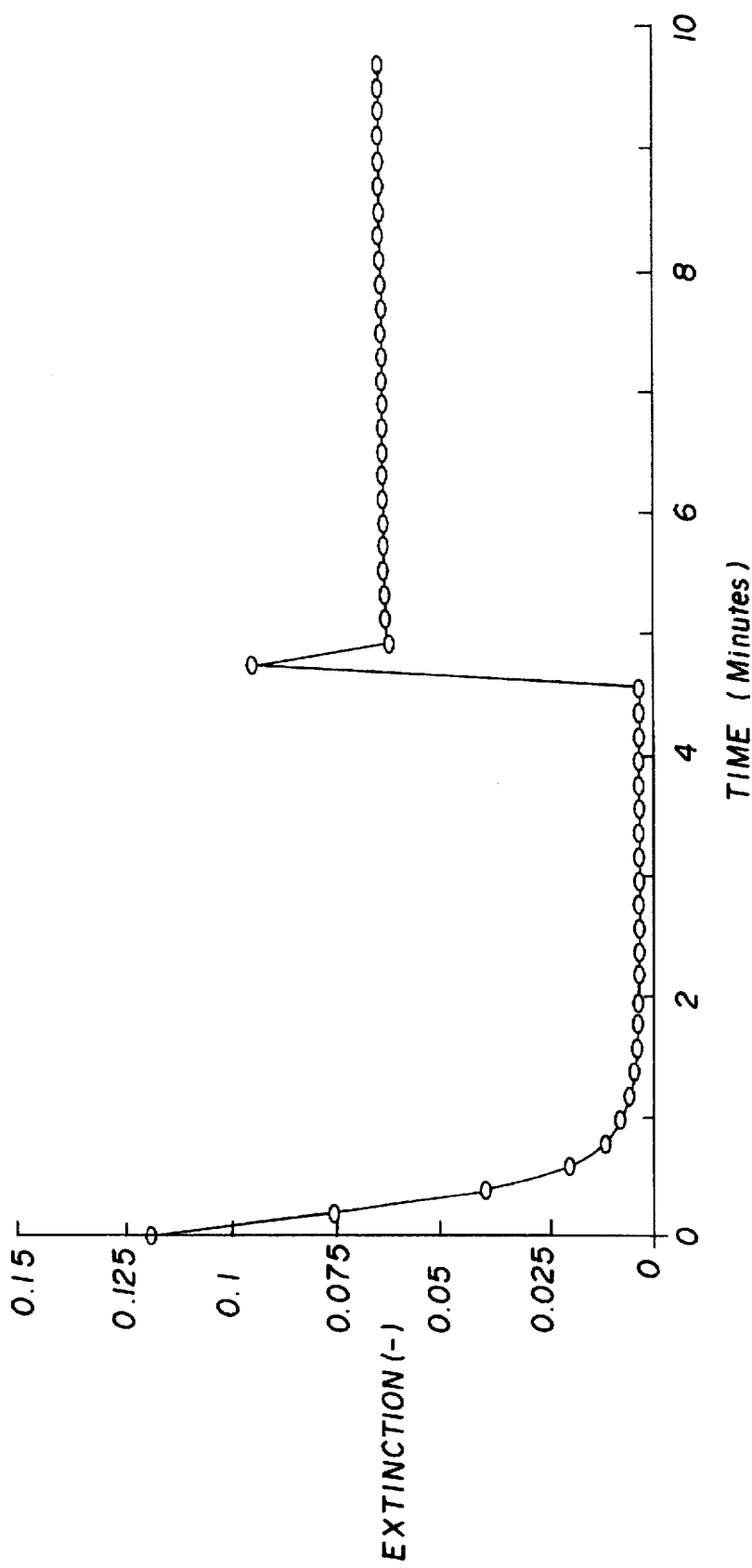
FIG. 4 shows the clearing of a naturally occuring lipaemic human serum by Lutensol® ON 50 as described in example 4.

We claim:

1. A method for the determination of iron in a biological sample, comprising the steps of:

adding a protein denaturing agent consisting essentially of urea or a urea derivative, and a detergent, wherein said detergent is a fatty alcohol polyglycol ether, and wherein said fatty alcohol polyglycol ether contains 4.5–6 ethoxy units, to said biological sample to release any bound iron, thereafter reducing any released iron to $Fe^{2+}$, adding a color reagent solution to said sample, and thereafter photometrically measuring any resulting color complex as an indication of the iron present in said biological sample.

2. The method according to claim 1, wherein the fatty alcohol polyglycol ether contains 5 to 6 ethoxy units.

3. The method according to claim 1, wherein the fatty alcohol polyglycol ether contains a branched or unbranched fatty alcohol residue which contains 9–11 carbon atoms.

4. The method according to claim 1, wherein the fatty alcohol polyglycol ether in said protein denaturing agent is at a concentration of at least 10 g/l.

5. The method according to claim 4, wherein said fatty alcohol polyglycol ether is at a concentration of 50 to 100 g/l.

6. The method according to claim 1, wherein said urea derivative is a guanidinium salt.

7. The method according to claim 6, wherein said guanidinium salt is selected from the group consisting of guanidinium chloride, guanidinium acetate, guanidinium thiocyanate and guanidinium sulfate.

8. The method according to claim 6, wherein said guanidinium salt is at a concentration of between 1 to 8 mol/l.

9. The method according to claim 1, wherein said released iron is reduced with an agent selected from the group consisting of ascorbic acid, dithionite and hydroxylamine.

10. The method according to claim 1, wherein said color reagent solution contains a complexing agent selected from the group consisting of bathophenantroline, ferene and ferrozine.

11. The method according to claim 1, wherein said determination of iron is carried out in an automated analyzer.

12. The method according to claim 1, wherein said biological sample is buffered to a pH between 3.5 and 6.

13. The method according to claim 12, wherein said biological sample is buffered with an acetate buffer.

14. A method for avoiding interference by lipaemia and gammopathy in the photometric determination of iron in a liquid sample, comprising the steps of:

adding a protein denaturing agent, consisting essentially of urea or a urea derivative, and detergent, wherein said detergent is a fatty alcohol polyglycol ether, and wherein said fatty alcohol polyglycol ether contains 4.5–6 ethoxy units, to said sample to release any bound iron, thereafter reducing any released iron to Fe2+, adding a color reagent solution to said sample, and thereafter photometrically measuring any resulting color complex, wherein said protein denaturing agent clears or reduces the turbidity of said sample prior to said photometric measurement.

15. A kit for the determination of iron in a biological sample, comprising the following reagents in separate containers:

a first reagent comprising a protein denaturing agent consisting essentially of urea or a urea derivative, and a detergent, wherein said detergent is a fatty alcohol polyglycol ether, and wherein said fatty alcohol polyglycol ether contains 4.5–6 ethoxy units, and a second reagent comprising a dye in the form of an aqueous solution or a dry mixture.

16. The kit according to claim 15, wherein said protein denaturing agent is at a concentration of 1 to 8 mol/l, said fatty alcohol polyglycol ether is at a concentration of at least 10 g/l and said dye is at a concentration of 0.5 to 50 mmol/l.

17. The kit according to claim 16, wherein said second reagent further comprises 40 to 200 mmol/l of a reducing agent.

18. The kit according to claim 15, further comprising a third reagent containing a reducing agent selected from the group consisting of ascorbic acid, dithionite and hydroxylamine.

* * * * *